(12) United States Patent
Childers et al.

(10) Patent No.: US 8,172,789 B2
(45) Date of Patent: *May 8, 2012

(54) PERITONEAL DIALYSIS SYSTEM HAVING CASSETTE-BASED-PRESSURE-CONTROLLED PUMPING

(75) Inventors: Robert W. Childers, New Port Richey, FL (US); Vital Eerlingen, Leuven (BE); Patrick Balteau, Bothey (BE); Duane Belongie, Minneapolis, MN (US)

(73) Assignee: Baxter International Inc., Deerfiled, IL (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/903,820

(22) Filed: Oct. 13, 2010

(65) Prior Publication Data

US 2011/0028892 A1    Feb. 3, 2011

Related U.S. Application Data

(60) Continuation of application No. 12/408,432, filed on Mar. 20, 2009, which is a continuation of application No. 10/446,068, filed on May 27, 2003, now Pat. No. 7,507,220, which is a division of application No. 10/078,568, filed on Feb. 14, 2002, now Pat. No. 6,592,542, which is a continuation of application No. 09/501,778, filed on Feb. 10, 2000, now Pat. No. 6,497,676.

(51) Int. Cl.
*A61M 1/00* (2006.01)
(52) U.S. Cl. .......................... 604/29; 604/5.01
(58) Field of Classification Search ............... 604/28, 604/29, 5.01–5.04, 19, 27, 4.01
See application file for complete search history.

(56) References Cited

U.S. PATENT DOCUMENTS 2,286,613 A    1/1942 Fuller
(Continued)

FOREIGN PATENT DOCUMENTS

EP    0 028 371    5/1981
(Continued)

OTHER PUBLICATIONS

Bergstrom et al., An Automated Apparatus for Peritoneal Dialysis with Volumetric Fluid Balance Measurement, reprinted from Dialysis & Transplantation, Jun./Jul. 1976.

(Continued)

*Primary Examiner* — Matthew F Desanto
(74) *Attorney, Agent, or Firm* — K&L Gates LLP

(57) ABSTRACT

A peritoneal dialysis system includes a removable cassette defining a flexible pump chamber and a pressure sensing area that is fluidly connected to the pump chamber wherein, during operation of the peritoneal dialysis system, peritoneal dialysis fluid is contained in the pump chamber; and a peritoneal dialysis machine configured to secure the removable cassette, peritoneal dialysis machine including (i) a pressure sensor positioned to align with and to contact the pressure sensing area of the removable cassette when the removable cassette is secured to the peritoneal dialysis machine, and (ii) a controller connected to the pressure sensor and adapted to change the operation of the peritoneal dialysis machine in response to changes in pressure sensed by the pressure sensor, wherein the pressure sensor and the pressure sensing area are arranged so that the pressure sensor measures a pressure of fluid in a fluid passage between the pump chamber and a patient during operation of the peritoneal dialysis system.

20 Claims, 8 Drawing Sheets

U.S. PATENT DOCUMENTS

| | | |
|---|---|---|
| 3,327,115 A | 1/1967 | Barlett |
| 3,485,245 A | 12/1969 | Lahr et al. |
| 3,620,215 A | 11/1971 | Tysk et al. |
| 3,626,670 A | 12/1971 | Pecker |
| 3,656,873 A | 4/1972 | Schiff |
| 3,689,204 A | 9/1972 | Prisk |
| 3,703,959 A | 11/1972 | Raymond |
| 3,707,967 A | 1/1973 | Kitrilakis et al. |
| 3,709,222 A | 1/1973 | DeVries |
| 3,792,643 A | 2/1974 | Scheafer |
| 3,902,490 A | 9/1975 | Jacobsen |
| 3,955,901 A | 5/1976 | Hamilton |
| 3,976,574 A | 8/1976 | White |
| 3,979,284 A | 9/1976 | Granger |
| 4,086,653 A | 4/1978 | Gernes |
| 4,126,132 A | 11/1978 | Portner et al. |
| 4,140,118 A | 2/1979 | Jassawalla |
| 4,142,524 A | 3/1979 | Jassawalla et al. |
| 4,158,530 A | 6/1979 | Bernstein |
| 4,181,245 A | 1/1980 | Garrett et al. |
| 4,187,057 A | 2/1980 | Xanthopoulos |
| 4,199,307 A | 4/1980 | Jassawalla |
| 4,235,231 A | 11/1980 | Schindler et al. |
| 4,236,880 A | 12/1980 | Archibald |
| 4,252,651 A | 2/1981 | Soderstrom |
| 4,265,601 A | 5/1981 | Mandoian |
| 4,273,121 A | 6/1981 | Jassawalla |
| 4,277,226 A | 7/1981 | Archibald |
| 4,303,376 A | 12/1981 | Siekmann |
| 4,310,141 A | 1/1982 | Tamura |
| 4,316,466 A | 2/1982 | Babb |
| 4,375,346 A | 3/1983 | Kraus et al. |
| 4,381,003 A | 4/1983 | Buoncristiani |
| 4,381,005 A | 4/1983 | Bujan |
| 4,382,753 A | 5/1983 | Archibald |
| 4,391,600 A | 7/1983 | Archibald |
| 4,410,322 A | 10/1983 | Archibald |
| 4,430,048 A | 2/1984 | Fritsch |
| 4,456,218 A | 6/1984 | Kawabata et al. |
| 4,468,222 A | 8/1984 | Lundquist |
| 4,479,760 A | 10/1984 | Bilstad et al. |
| 4,479,761 A | 10/1984 | Bilstad et al. |
| 4,479,762 A | 10/1984 | Bilstad et al. |
| 4,504,038 A | 3/1985 | King |
| 4,530,759 A | 7/1985 | Schal |
| 4,552,552 A | 11/1985 | Polaschegg et al. |
| 4,559,036 A | 12/1985 | Wunsch |
| 4,559,044 A | 12/1985 | Robinson et al. |
| 4,560,472 A | 12/1985 | Granzow et al. |
| 4,585,436 A | 4/1986 | Davis et al. |
| 4,613,327 A | 9/1986 | Tegrarian et al. |
| 4,618,343 A | 10/1986 | Polaschegg |
| RE32,303 E | 12/1986 | Lasker et al. |
| 4,634,430 A | 1/1987 | Polaschegg |
| 4,639,245 A | 1/1987 | Pastrone et al. |
| 4,642,098 A | 2/1987 | Lundquist |
| 4,648,810 A | 3/1987 | Schippers et al. |
| 4,648,872 A | 3/1987 | Kamen |
| 4,657,490 A | 4/1987 | Abbott |
| 4,694,848 A | 9/1987 | Jorgensen et al. |
| 4,703,773 A | 11/1987 | Hansen et al. |
| 4,717,117 A | 1/1988 | Cook |
| 4,718,890 A | 1/1988 | Peabody |
| 4,747,822 A | 5/1988 | Peabody |
| 4,769,134 A | 9/1988 | Allan et al. |
| 4,778,356 A | 10/1988 | Hicks |
| 4,778,451 A | 10/1988 | Kamen |
| 4,784,576 A | 11/1988 | Bloom et al. |
| 4,808,161 A | 2/1989 | Kamen |
| 4,816,019 A | 3/1989 | Kamen |
| 4,818,186 A | 4/1989 | Pastrone et al. |
| 4,818,190 A | 4/1989 | Pelmulder et al. |
| 4,823,552 A | 4/1989 | Ezell et al. |
| 4,826,482 A | 5/1989 | Kamen |
| 4,828,545 A | 5/1989 | Epstein et al. |
| 4,830,586 A | 5/1989 | Herter et al. |
| 4,842,582 A | 6/1989 | Mahurkar |
| 4,842,584 A | 6/1989 | Pastrone |
| 4,848,722 A | 7/1989 | Webster |
| 4,850,805 A | 7/1989 | Madsen et al. |
| 4,852,851 A | 8/1989 | Webster |
| 4,855,356 A | 8/1989 | Holub et al. |
| 4,859,319 A | 8/1989 | Borsari |
| 4,865,584 A | 9/1989 | Epstein et al. |
| 4,872,813 A | 10/1989 | Gorton et al. |
| 4,886,432 A | 12/1989 | Kimberlin |
| 4,927,411 A | 5/1990 | Pastrone et al. |
| 4,942,735 A | 7/1990 | Mushika et al. |
| 5,002,471 A | 3/1991 | Perlov |
| 5,006,050 A | 4/1991 | Cooke et al. |
| 5,062,774 A | 11/1991 | Kramer et al. |
| 5,088,515 A | 2/1992 | Kamen |
| 5,094,820 A | 3/1992 | Maxwell et al. |
| 5,098,262 A | 3/1992 | Wrecker et al. |
| 5,108,844 A | 4/1992 | Blumberg et al. |
| 5,125,891 A | 6/1992 | Hossain et al. |
| 5,141,493 A | 8/1992 | Jacobsen et al. |
| 5,163,900 A | 11/1992 | Wortrich |
| 5,176,956 A | 1/1993 | Jevne et al. |
| 5,178,182 A | 1/1993 | Kamen |
| 5,185,084 A | 2/1993 | Lapidus et al. |
| 5,195,960 A | 3/1993 | Hossain et al. |
| 5,207,642 A | 5/1993 | Orkin et al. |
| 5,241,985 A | 9/1993 | Faust et al. |
| 5,245,693 A | 9/1993 | Ford et al. |
| 5,247,434 A | 9/1993 | Peterson et al. |
| 5,252,044 A | 10/1993 | Raines et al. |
| 5,292,306 A | 3/1994 | Wynkoop et al. |
| 5,302,093 A | 4/1994 | Owens et al. |
| 5,316,452 A | 5/1994 | Bogen et al. |
| 5,332,372 A | 7/1994 | Reynolds |
| 5,344,292 A | 9/1994 | Rabenau et al. |
| 5,350,357 A | 9/1994 | Kamen et al. |
| 5,378,126 A | 1/1995 | Abrahamson et al. |
| 5,389,243 A | 2/1995 | Kaplan |
| 5,397,222 A | 3/1995 | Moss et al. |
| 5,409,355 A | 4/1995 | Brooke |
| 5,415,528 A | 5/1995 | Ogden et al. |
| 5,421,208 A | 6/1995 | Packard et al. |
| 5,421,823 A | 6/1995 | Kamen et al. |
| 5,429,485 A | 7/1995 | Dodge |
| 5,431,626 A | 7/1995 | Bryant et al. |
| 5,458,468 A | 10/1995 | Ye et al. |
| 5,474,683 A | 12/1995 | Bryant et al. |
| 5,476,368 A | 12/1995 | Rabenau et al. |
| 5,482,440 A | 1/1996 | Dennehey et al. |
| 5,487,649 A | 1/1996 | Dorsey, III et al. |
| 5,522,769 A | 6/1996 | DeGuiseppi |
| 5,526,844 A | 6/1996 | Kamen |
| 5,533,389 A | 7/1996 | Kamen et al. |
| 5,536,412 A | 7/1996 | Ash |
| 5,542,919 A | 8/1996 | Simon et al. |
| 5,554,013 A | 9/1996 | Owens et al. |
| 5,556,263 A | 9/1996 | Jacobsen et al. |
| 5,570,716 A | 11/1996 | Kamen et al. |
| 5,575,310 A | 11/1996 | Kamen et al. |
| 5,578,012 A | 11/1996 | Kamen et al. |
| 5,580,460 A | 12/1996 | Polaschegg |
| 5,586,868 A | 12/1996 | Lawless et al. |
| 5,588,816 A | 12/1996 | Abbott et al. |
| 5,591,344 A | 1/1997 | Kenley et al. |
| 5,603,354 A | 2/1997 | Jacobsen et al. |
| 5,609,572 A | 3/1997 | Lang |
| 5,620,312 A | 4/1997 | Hyman et al. |
| 5,628,908 A | 5/1997 | Kamen et al. |
| 5,630,935 A | 5/1997 | Treu |
| 5,632,606 A | 5/1997 | Jacobsen et al. |
| 5,634,896 A | 6/1997 | Bryant et al. |
| 5,645,734 A | 7/1997 | Kenley et al. |
| 5,669,764 A | 9/1997 | Behringer et al. |
| 5,718,692 A | 2/1998 | Schon et al. |
| 5,722,947 A | 3/1998 | Jeppsson et al. |
| 5,758,563 A | 6/1998 | Robinson |
| 5,788,671 A | 8/1998 | Johnson |
| 5,790,752 A | 8/1998 | Anglin et al. |
| 5,807,075 A | 9/1998 | Jacobsen et al. |
| 5,814,004 A | 9/1998 | Tamari |

| | | | |
|---|---|---|---|
| 5,816,779 | A | 10/1998 | Lawless et al. |
| 5,836,908 | A | 11/1998 | Beden et al. |
| 5,871,566 | A | 2/1999 | Rutz |
| 5,919,369 | A | 7/1999 | Ash |
| 5,921,951 | A | 7/1999 | Morris |
| 5,924,975 | A | 7/1999 | Goldowsky |
| 5,931,647 | A | 8/1999 | Jacobsen et al. |
| 5,938,634 | A * | 8/1999 | Packard .................. 604/29 |
| 5,944,495 | A | 8/1999 | Jacobsen et al. |
| 5,944,684 | A | 8/1999 | Roberts et al. |
| 5,965,433 | A | 10/1999 | Gardetto et al. |
| 5,989,423 | A | 11/1999 | Kamen et al. |
| 6,007,310 | A | 12/1999 | Jacobsen et al. |
| 6,017,194 | A | 1/2000 | North, Jr. |
| 6,030,359 | A | 2/2000 | Nowosielski |
| 6,036,668 | A | 3/2000 | Mathis |
| 6,041,801 | A | 3/2000 | Gray et al. |
| 6,065,941 | A | 5/2000 | Gray et al. |
| 6,126,403 | A | 10/2000 | Yamada |
| 6,129,699 | A | 10/2000 | Haight et al. |
| 6,165,154 | A | 12/2000 | Gray et al. |
| 6,208,107 | B1 | 3/2001 | Maske et al. |
| 6,210,361 | B1 | 4/2001 | Kamen et al. |
| 6,223,130 | B1 | 4/2001 | Gray et al. |
| 6,228,047 | B1 | 5/2001 | Dadson |
| 6,231,320 | B1 | 5/2001 | Lawless et al. |
| 6,234,991 | B1 | 5/2001 | Gorsuch |
| 6,234,997 | B1 | 5/2001 | Kamen et al. |
| 6,245,039 | B1 | 6/2001 | Brugger et al. |
| 6,248,093 | B1 | 6/2001 | Moberg |
| 6,254,567 | B1 | 7/2001 | Treu et al. |
| 6,270,673 | B1 | 8/2001 | Belt et al. |
| 6,280,408 | B1 | 8/2001 | Sipin |
| 6,302,653 | B1 | 10/2001 | Bryant et al. |
| 6,343,614 | B1 | 2/2002 | Gray et al. |
| 6,364,857 | B1 | 4/2002 | Gray et al. |
| 6,382,923 | B1 | 5/2002 | Gray |
| 6,416,293 | B1 | 7/2002 | Bouchard et al. |
| 6,491,656 | B1 * | 12/2002 | Morris .................. 604/6.09 |
| 6,491,658 | B1 | 12/2002 | Miura et al. |
| 6,497,676 | B1 | 12/2002 | Childers et al. |
| 6,595,948 | B2 | 7/2003 | Suzuki et al. |
| 6,743,201 | B1 | 6/2004 | Dönig et al. |
| 6,814,547 | B2 | 11/2004 | Childers et al. |
| 6,949,079 | B1 | 9/2005 | Westberg et al. |
| 7,004,924 | B1 | 2/2006 | Brugger et al. |
| 2001/0018937 | A1 | 9/2001 | Nemoto |
| 2002/0045851 | A1 | 4/2002 | Suzuki et al. |

FOREIGN PATENT DOCUMENTS

| | | |
|---|---|---|
| EP | 0 033 096 | 8/1981 |
| EP | 0 052 004 | 5/1982 |
| EP | 0 097 432 | 1/1984 |
| EP | 0 157 024 | 10/1985 |
| EP | 0 206 195 | 12/1986 |
| EP | 0 319 272 | 6/1989 |
| EP | 0 402 505 | 12/1990 |
| EP | 0 660 725 | 7/1995 |
| GB | 1 326 236 | 8/1973 |
| WO | 85/04813 | 11/1985 |
| WO | 86/01115 | 2/1986 |
| WO | 87/05223 | 9/1987 |
| WO | 89/01795 | 3/1989 |
| WO | 90/13795 | 11/1990 |
| WO | 94/20158 | 9/1994 |
| WO | 03/099355 | 12/2003 |

OTHER PUBLICATIONS

Bran & Luebbe GmbH, Diaphragm Metering Pumps, Chem. Eng'g Progress, Apr. 1987, at 18-24.
Brochure entitled Fresenius Delivers 90/2 Peritoneal Therapy Cycler (Apr. 2001).
Brochure entitled, AP Hauni: Automatisches Peritonealdialyse-Great (1970).
Brochure entitled, For Volume Measurement, Temperature Control and Cycling of Dialysing Fluid, Peritoneal Dialyser PD700, 1970.
Brochure entitled, Peritoneal Dialyser PD700, May 1979.
Brochure entitled, SIF 901 Perugia, admitted prior art.
Defendants' Final Invalidity Contentions for U.S. Patent No. 6,814,547, *Baxter Healthcare Corporation v. Fresenius Medical Care Holdings*, Case No. C 07-01359 PJH (JL), filed Apr. 1, 2009.
Defendants' Preliminary Invalidity Contentions for U.S. Patent No. 6,814,547, *Baxter Healthcare Corporation v. Fresenius Medical Care Holdings*, Case No. C 07-01359 PJH (JL), filed Jan. 31, 2008.
Document entitled 90/2 Cycler Software, Version 3.96 (Jan. 24, 1992).
Drukker et al., Replacement of Renal Function by Dialysis, 2nd Ed., Ch. 21, 1983.
Elsevier Science Ltd., Air-Operated Diaphragm Pumps, World Pumps, Jan. 1996, at 38.
Expert Witness Report of Ronald J. Adrian Regarding Lack of Written Description, Lack of Enablement, and Indefiniteness of the Asserted Claim (Claim 12) of U.S. Patent No. 6,814,547, Apr. 24, 2009.
Fresenius Delivers 90/2 Peritoneal Therapy Cycler (on information and belief, on sale in United States by 1991).
Fresenius Freedom Cycler Operating Instructions, admitted prior art.
Fresenius USA/Delmed 90/2 Peritoneal Dialysis System Operators Manual, dated Feb. 6, 1991.
Memorandum of Donald X. Vaccarino entitled 90/2 History File (1991-1992).
Operating Instructions, Peritoneal Dialyser PD700, For Ser. No. 300.
Operator's Instructions, Fresenius 90/2 Peritoneal Therapy Cycler (Rev. C. copyright 1991-2000).
PD700 Peritoneal Dialyser Users Hand-book, Dec. 1977.
Peritoneal Dialyser PD700 Instruction Manual, admitted prior art.
Peritoneal Dialyser PD700 Service Manual, Jun. 1977.
Technical Note, PD700 Peritoneal Dialyser, Jan. 29, 1979.
Translation of brochure entitled, SIF 901 Perugia, admitted prior art.
Translation of Certificate for translation of brochure entitled, SIF 901 Perugia, admitted prior art.
W.M. Phillips, J.A. Brighton & W.S. Pierce, Artificial Heart Evaluation Using Flow Visualization Techniques, published in Transactions: American Society for Artificial Internal Organs, vol. XVIII (1972).
Non-Final Office Action for U.S. Appl. No. 10/155,754 mailed Sep. 11, 2003.
Final Office Action for U.S. Appl. No. 10/155,754 mailed Mar. 24, 2004.
Non-Final Office Action for U.S. Appl. No. 11/614,850 mailed May 13, 2009.
Final Office Action for U.S. Appl. No. 11/614,850 mailed Mar. 18, 2010.
Non-Final Office Action for U.S. Appl. No. 11/614,858 mailed May 13, 2010.
Non-Final Office Action for U.S. Appl. No. 11/617,527 mailed Nov. 24, 2008.
Final Office Action for U.S. Appl. No. 11/617,527 mailed May 5, 2009.
Non-Final Office Action for U.S. Appl. No. 11/617,527 mailed Aug. 12, 2009.
Final Office Action for U.S. Appl. No. 11/617,527 mailed Jan. 21, 2010.
Non-Final Office Action for U.S. Appl. No. 11/617,527 mailed Jul. 16, 2010.
Non-Final Office Action for U.S. Appl. No. 10/446,068 mailed May 12, 2006.
Final Office Action for U.S. Appl. No. 10/446,068 mailed Nov. 7, 2006.
Non-Final Office Action for U.S. Appl. No. 10/446,068 mailed Sep. 7, 2007.
Final Office Action for U.S. Appl. No. 10/446,068 mailed Feb. 28, 2008.
Final Office Action for U.S. Appl. No. 10/446,068 mailed Jul. 31, 2008.
Non-Final Office Action for U.S. Appl. No. 10/446,068 mailed Nov. 14, 2008.
Non-Final Office Action for U.S. Appl. No. 11/773,787 mailed Jul. 28, 2010.
Non-Final Office Action for U.S. Appl. No. 12/506,738 mailed Jun. 24, 2011.

Non-Final Office Action for U.S. Appl. No. 12/903,902 mailed Jul. 6, 2011.

Non-Final Office Action for U.S. Appl. No. 12/903,887 mailed Jul. 6, 2011.

Non-Final Office Action for U.S. Appl. No. 11/773,148 mailed May 17, 2010.

Final Office Action for U.S. Appl. No. 11/773,148 mailed Feb. 7, 2011.

Non-Final Office Action for U.S. Appl. No. 12/408,432 mailed Mar. 3, 2011.

Non-Final Office Action for U.S. Appl. No. 11/617,543 mailed Sep. 24, 2007.

Final Office Action for U.S. Appl. No. 11/617,543 mailed May 30, 2008.

Non-Final Office Action for U.S. Appl. No. 11/617,543 mailed Oct. 20, 2008.

Final Office Action for U.S. Appl. No. 11/617,543 mailed Jul. 22, 2009.

Non-Final Office Action for U.S. Appl. No. 12/987,738 mailed Apr. 29, 2011.

* cited by examiner

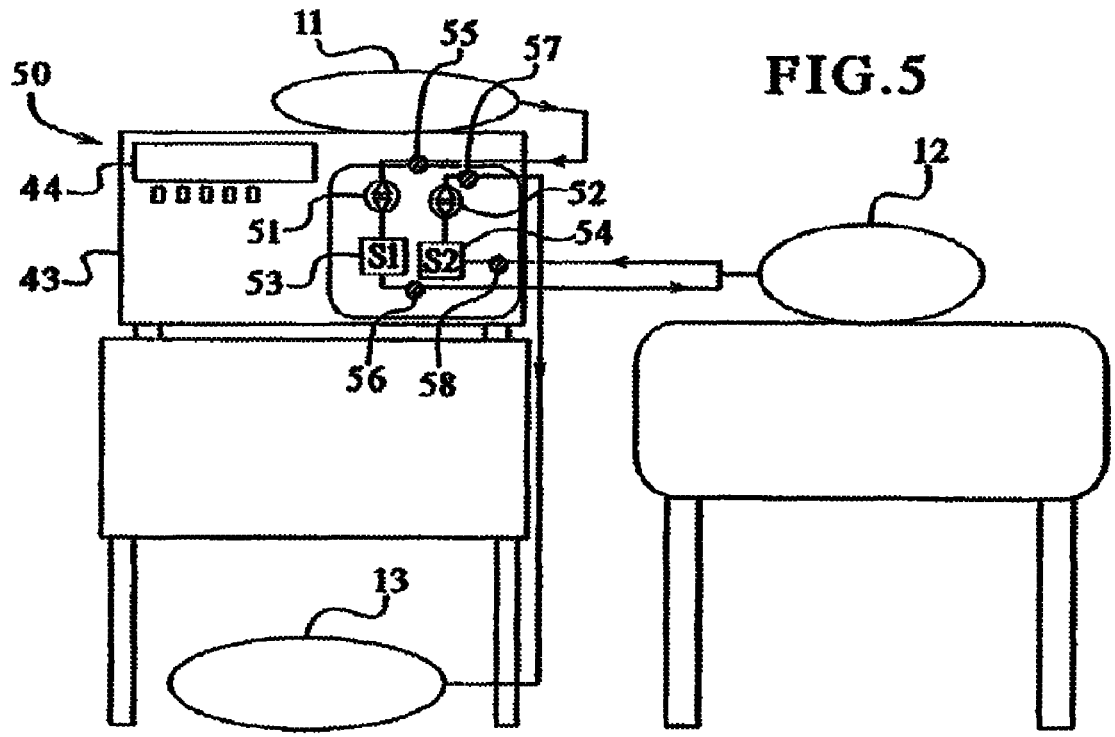
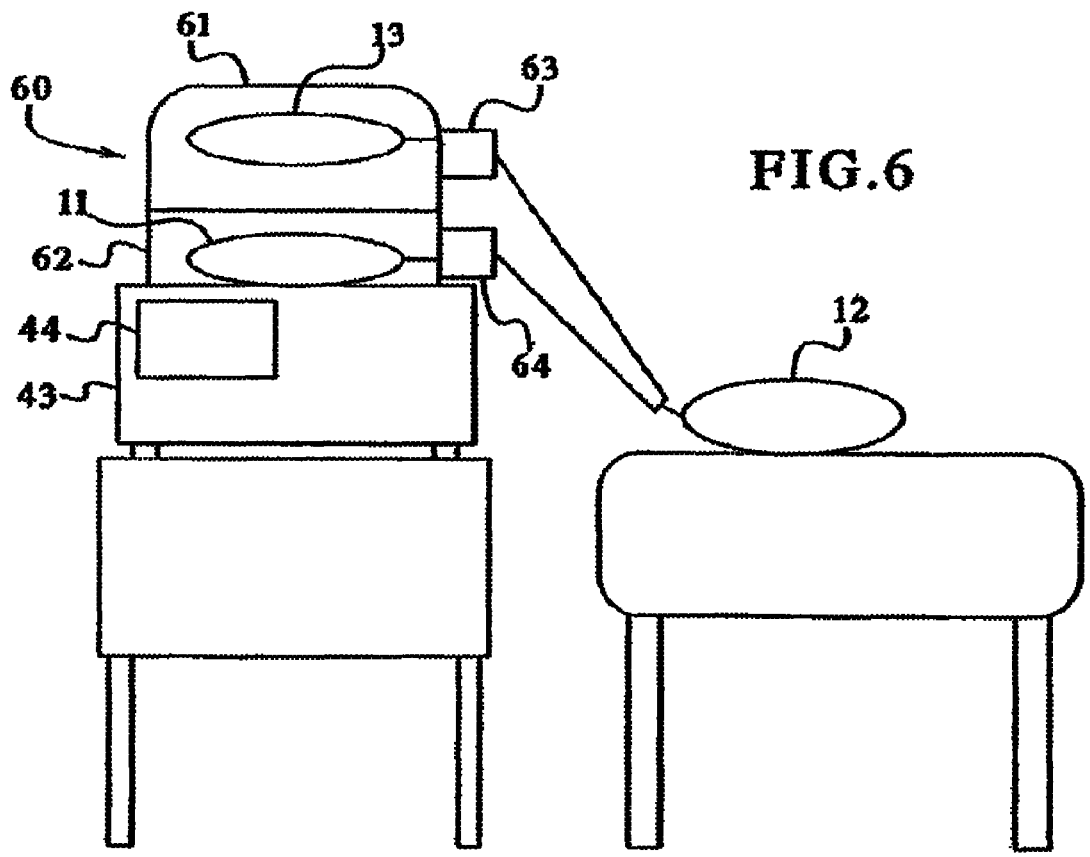

PERITONEAL DIALYSIS SYSTEM HAVING CASSETTE-BASED-PRESSURE-CONTROLLED PUMPING

PRIORITY CLAIM

This application claims priority to and the benefit as a continuation of U.S. patent application Ser. No. 12/408,432, filed Mar. 20, 2009, which is a continuation of U.S. patent application Ser. No. 10/446,068, filed May 27, 2003, which is a divisional application of U.S. patent application Ser. No. 10/078,568, filed Feb. 14, 2002, issued as U.S. Pat. No. 6,592,542, which is a continuation of U.S. patent application Ser. No. 09/501,778, filed Feb. 10, 2000, issued as U.S. Pat. No. 6,497,676, the entire contents of each of which are incorporated herein by reference and relied upon.

BACKGROUND

The present invention relates generally to the treatment of end stage renal disease. More specifically, the present invention relates to methods and apparatus for monitoring the performance of peritoneal dialysis.

Using dialysis to support a patient whose renal function has decreased to the point where the kidneys no longer sufficiently function is known. Two principal dialysis methods are utilized: hemodialysis; and peritoneal dialysis.

In hemodialysis, the patient's blood is passed through an artificial kidney dialysis machine. A membrane in the machine acts as an artificial kidney for cleansing the blood. Because it is an extracorporeal treatment that requires special machinery, certain inherent disadvantages exist with hemodialysis.

To overcome the disadvantages associated with hemodialysis; peritoneal dialysis was developed. Peritoneal dialysis utilizes the patient's own peritoneum as a semi-permeable membrane. The, peritoneum is a membranous lining of the abdominal body cavity. Due to good perfusion, the peritoneum is capable of acting as a natural semi-permeable membrane.

Peritoneal dialysis periodically infuses sterile aqueous solution into the peritoneal cavity. This solution is called peritoneal dialysis solution, or dialysate. Diffusion and osmosis exchanges take place between the solution and the blood stream across the natural body membranes. These exchanges remove the waste products that the kidneys normally excrete. The waste products typically consist of solutes like urea and creatinine. The kidneys also maintain the levels of other substances such as sodium and water which need to be regulated by dialysis. The diffusion of water and solutes across the peritoneal membrane during dialysis is called ultrafiltration.

In continuous ambulatory peritoneal dialysis, a dialysis solution is introduced into the peritoneal cavity utilizing a catheter. An exchange of solutes between the dialysate and the blood is achieved by diffusion. Further removal is achieved by providing a suitable osmotic gradient from the blood to the dialysate to permit water outflow from the blood. This allows a proper acid-base, electrolyte and fluid balance to be achieved in the body. The dialysis solution is simply drained from the body cavity through the catheter.

Peritoneal dialysis raises a number of concerns including: the danger of peritonitis; a lower efficiency and therefore increased duration of dialysis hours compared to hemodialysis; and costs incurred when automated equipment is utilized.

A number of variations on peritoneal dialysis have been explored. One such variation is automated peritoneal dialysis ("APD"). APD uses a machine, called a cycler, to automatically infuse, dwell, and drain peritoneal dialysis solution to and from the patient's peritoneal cavity. APD is particularly attractive to a peritoneal dialysis patient, because it can be performed at night while the patient is asleep. This frees the patient from the day-to-day demands of continuous ambulatory peritoneal dialysis during his/her waking and working hours.

The APD sequence typically lasts for several hours. It often begins with an initial drain cycle to empty the peritoneal cavity of spent dialysate. The APD sequence then proceeds through a succession of fill, dwell, and drain phases that follow one after the other. Each fill/dwell/drain sequence is called a cycle. APD can be and is practiced in a number of different ways.

Current APD systems do not monitor the patient intraperitoneal pressure during a therapy session. Current systems simply limit the external pressure (or suction) that a pump can apply to the line or lumen that is attached to the patient catheter. If the patient is located below the system, sometimes referred to as a cycler, a gravity head will add to the positive fill pressure that the cycler can apply to the patient catheter. Conversely, if the patient is located above the cycler, the gravity head will decrease from the positive fill pressure that the cycler can apply to the patient catheter.

The monitoring of intraperitoneal pressure would be useful because cyclers will sometimes not fully drain a patient between cycles. Specifically, currently-available cyclers are unable to determine whether a patient absorbed some fluid or whether some fluid is simply not able to be drained out because of the position of the patient or the catheter.

As a result, some currently-available systems utilize a minimum drain threshold to determine the amount of fluid that should be delivered to the patient during the next fill. For example, if 85% of the fill volume has been drained when the cycler determines that the patient is "empty", the next fill volume will be 100%. If only 80% were drained, the next fill volume would be limited to 95%.

A negative ultrafiltrate (uF) alarm will sound when the patient has retained more than a predetermined percentage of the fill volume. The predetermined percentage can typically be either 50% or 100% of the fill volume. However, the patient can override this alarm if he/she does not feel overfull. The number of times the patients can override the uF alarm during a single therapy may be limited by the software of the cycler. However, the uF alarm typically does not consider the actual ultrafiltrate that may also accumulate in the peritoneal cavity along with the dialysate.

Currently-available cyclers fill the patient to a specific, preprogrammed volume during each cycle. The doctor prescribes this fill volume based upon the patient's size, weight and other factors. However, because currently-available cyclers cannot monitor intraperitoneal pressure, the doctor cannot take this factor into account when formulating the prescription. It is also known that intraperitoneal pressure (IPP) has an effect on ultrafiltration (UF).

FIGS. 1-3 provide schematic illustrations of current APD cyclers. None of them attempt to monitor intraperitoneal pressure.

Referring to FIG. 1, a cycler 10a is illustrated which includes a dialysate container 11, a patient 12 and a drain container 13 are illustrated schematically. The infusion of dialysate from the container 11 into the patient 12 is caused by the gravitational head indicated at 14 while the draining of used dialysate from the patient 12 to the drain container 13 is caused by the drain head indicated at 15. The cycler 10a includes no sensors for monitoring the pressure inside the peritoneum of the patient 12. A single lumen 16 connects both the dialysate container 11 and drain container 13 to the patient 12. Valves 17, 18 operated by the cycler 10a control the flow of either dialysate from the container 11 to the patient 12 or waste material from the patient 12 to the drain container 13.

Turning to FIG. 2, in the cycler 10b, the drain container 13 and dialysate container 11 are contained within a pressurized chamber 19. The chamber 19 can be pressurized or evacuated to either fill or drain the patient. Again, the selective operation of valves 17, 18 control whether dialysate is being transferred to or from the patient 12. Again, no sensors are provided for detecting or monitoring intraperitoneal pressure of the patient 12.

Turning to FIG. 3, in the system 10c, a dialysate container 11 is connected to a pump 21 which, in turn, connects the dialysate container 11 to a common lumen or catheter 16 which is connected to the patient. A fluid flow control valve is provided at 23 and is controlled by the cycler 106. The drain container 13 is also connected to a pump 24 which, in turn, connects the drain container 13 to the lumen 16. A control valve is again provided at 25.

The drain and fill rates of the cyclers 10a-10c illustrated in FIGS. 1-3 are determined by the gravitational head (see FIG. 1) or the suction or pressure (see FIGS. 2 and 3) applied to the patient line 16. Typically, the cyclers 10a-10c fail to optimize either the fill rate or the drain rate because the pressure is either fixed by the gravitational head or the pressure or suction applied by the chamber 10b of FIG. 2 which occurs at the opposing end of the patient line 16. Thus, without measuring the intraperitoneal pressure or having a way to estimate the same, it is difficult to optimize either the drain or fill rate. In the case of the cycler 10c in FIG. 3, optimizing the drain or fill rate is guesswork due to the lack of any pressure reading at all.

Accordingly, there is a need for an improved cycler that measures patient intraperitoneal pressure during a therapy session, including both during the drain and the fill as well as the dwell. Further, there is a need for an improved cycler that measures intraperitoneal pressure and which would use that data to more completely drain a patient between cycles. Further, there is a need for an improved cycler which would accurately measure intraperitoneal pressure to avoid overfilling a patient. Finally, there is a need for an improved cycler which would monitor intraperitoneal pressure during both the fill and drain cycles to optimize the speed at which the patient is filled and drained and to therefore increase the dwell portion of a therapy session.

SUMMARY

The present invention satisfies the aforenoted needs by providing a system for providing peritoneal dialysis to a patient which comprises a dialysate container connected to the patient with a first pressure sensor connected in-line therebetween, and a drain container connected to the patient with a second pressure sensor connected in-line therebetween.

In an embodiment, the system further comprises a first pump disposed in-line between the dialysate container and the first pressure sensor.

In an embodiment, the dialysate flows from the dialysate container into the patient under a hydrostatic head.

In an embodiment, a second pump is disposed in-line between the drain container and the second pressure sensor.

In an embodiment, the dialysate flows from the patient to the drain container under a hydrostatic head.

In an embodiment, the second pressure sensor measures an intraperitoneal pressure of the patient while dialysate flows from the dialysate container to the patient.

In an embodiment, the first pressure sensor measures an intraperitoneal pressure of the patient while dialysate flows from the patient to the drain container.

In an embodiment, the system further comprises a first lumen connecting the dialysate container to the first sensor and the first sensor to a catheter, and a second lumen connecting the drain container to the second sensor and the second sensor to the catheter, the catheter being connected to the patient, a flow of dialysate from the patient to the drain container evacuating dialysate from the first lumen and causing said dialysate from the first lumen to flow through the second lumen and to the drain container.

In an embodiment, the catheter is a dual lumen catheter.

In an embodiment, the first and second sensors are redundant in-line pressure/vacuum sensors.

In an embodiment, the present invention provides a method for dialyzing a patient comprising the steps of: placing a catheter in a peritoneum of the patient; providing at least one dialysate container; connecting the dialysate container to the catheter with a first lumen that includes a first pressure sensor disposed in-line and between the catheter and the dialysate container; providing at least one drain container; connecting the drain container to the catheter with a second lumen that includes a second pressure sensor disposed in-line and between the catheter and the drain container; transferring dialysate from the dialysate container to the peritoneum of the patient and monitoring an intraperitoneal pressure of the patient with the second pressure sensor; and transferring dialysate from the peritoneum of the patient to the drain container and monitoring the intraperitoneal pressure of the patient with the first pressure sensor.

In an embodiment, the step of transferring dialysate from the dialysate container to the peritoneum of the patient further comprises pumping dialysate from the dialysate container to the patient with a first pump disposed in-line between the dialysate container and the first pressure sensor.

In an embodiment, the step of transferring dialysate from the peritoneum of the patient to the drain container further comprises pumping dialysate from the peritoneum of the patient to the drain container with a second pump disposed in-line between the drain container and the second pressure sensor.

In an embodiment, the dialysate container is disposed vertically above the peritoneum of the patient and the step of transferring dialysate from the dialysate container to the peritoneum of the patient further comprises flowing dialysate from the dialysate container to the patient under a hydrostatic head.

In an embodiment, the drain container is disposed vertically below the peritoneum of the patient and the step of transferring dialysate from the peritoneum of the patient to the drain container further comprises flowing dialysate from the peritoneum of the patient to the drain container under a hydrostatic head.

Additional features and advantages are described herein, and will be apparent from the following Detailed Description and the figures.

BRIEF DESCRIPTION OF THE FIGURES

FIG. 5 illustrates, schematically, a second embodiment of an automated peritoneal dialysis system made in accordance with the present invention;

FIG. 6 illustrates, schematically, a third embodiment of an automated peritoneal dialysis system made in accordance with the present invention;

It should be understood that the drawings are not necessarily to scale and that the embodiments are sometimes illustrated by graphic symbols, phantom lines, diagrammatic representations and fragmentary views. In certain instances, details which are not necessary for an understanding of the present invention or which render other details difficult to perceive may have been omitted. It should be understood, of course, that the invention is not necessarily limited to the particular embodiments illustrated herein.

DETAILED DESCRIPTION

Figure 1:
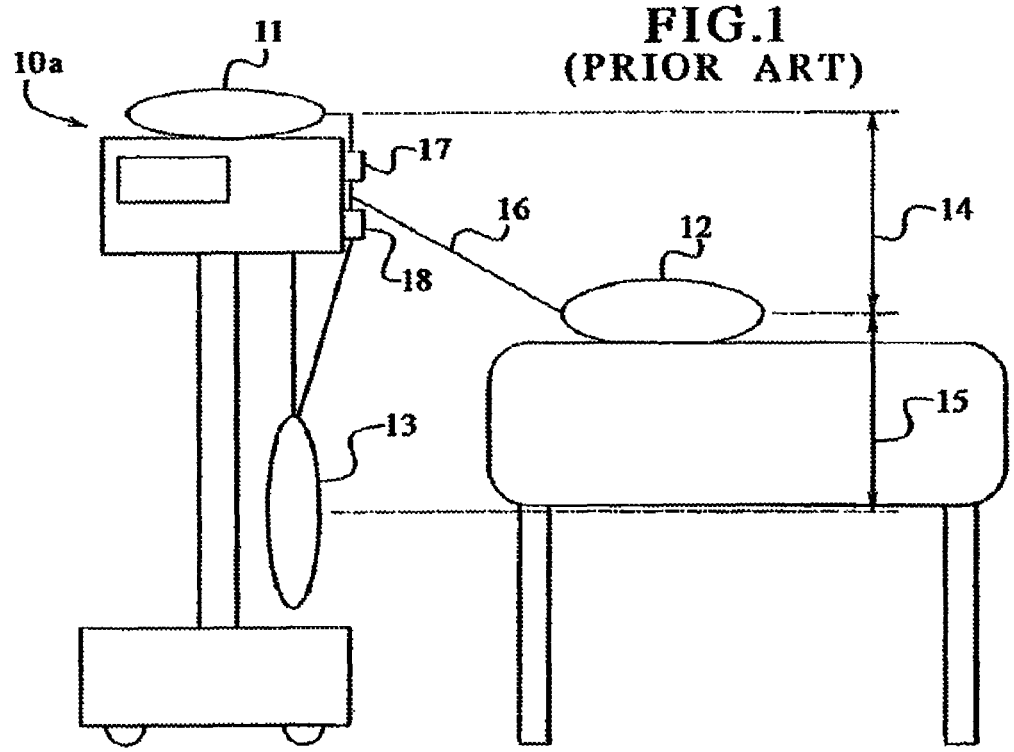
FIG. 1 illustrates, schematically, a prior art automated peritoneal dialysis system.
Figure 2:
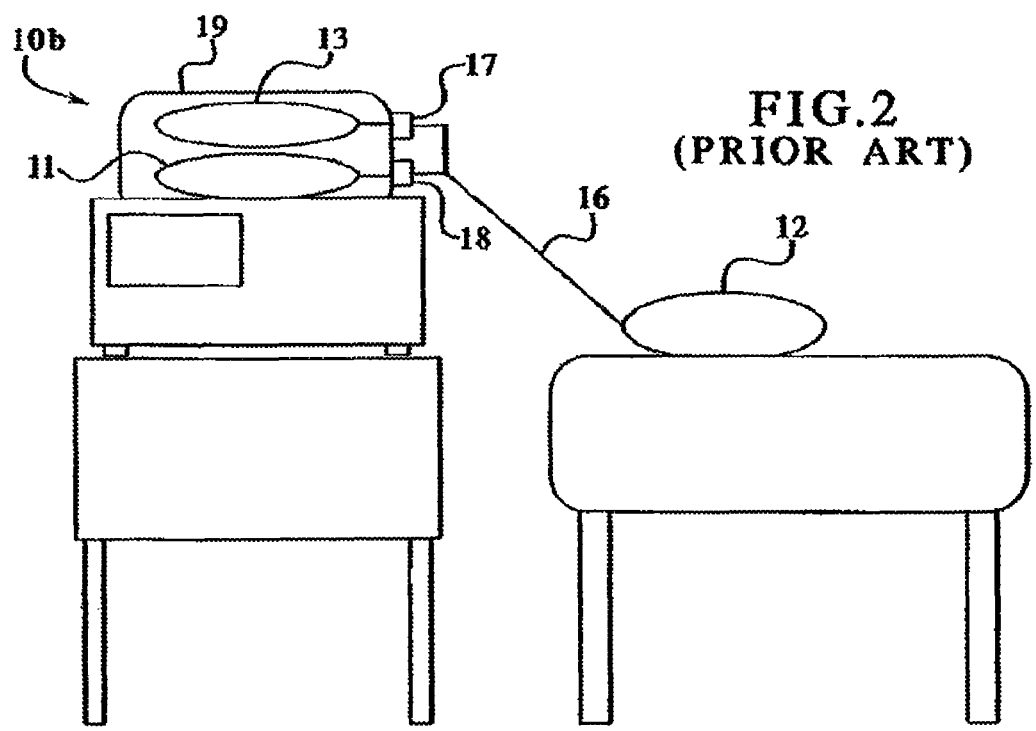
FIG. 2 illustrates, schematically, a prior art automated peritoneal dialysis system.
Figure 3:
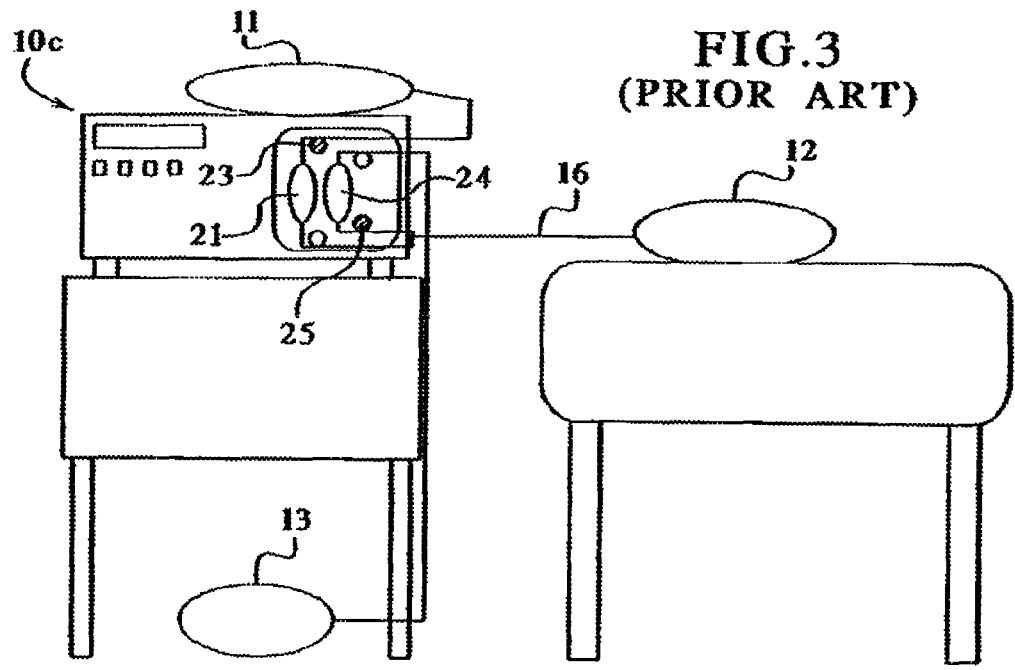
FIG. 3 illustrates, schematically, a prior art automated peritoneal dialysis system.
Figure 4:
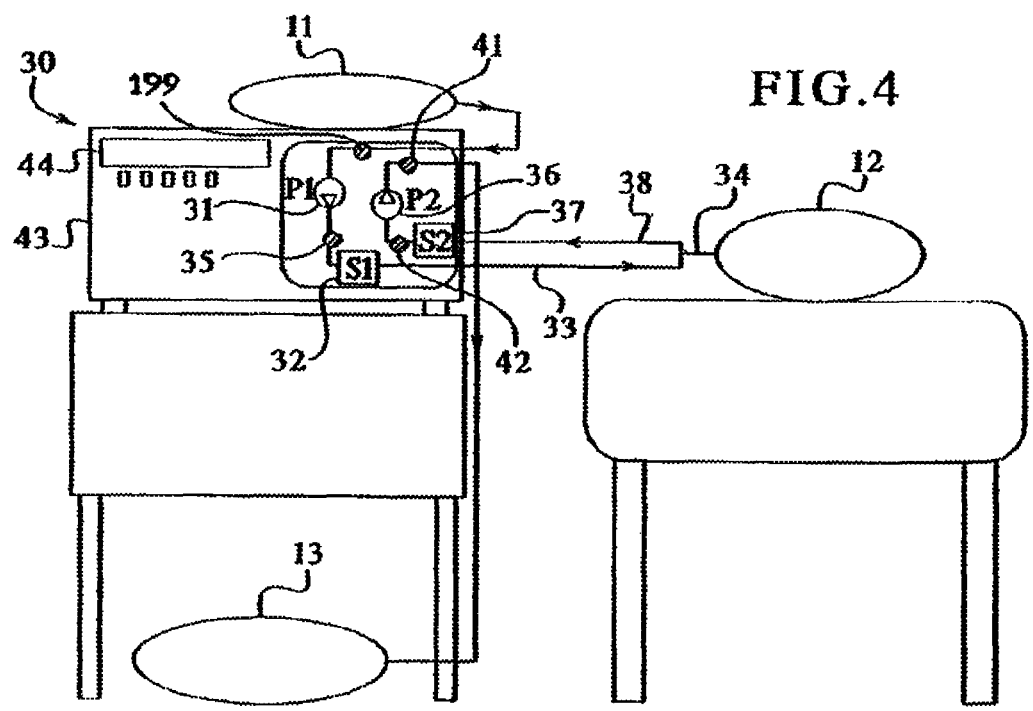
FIG. 4 illustrates, schematically, an automated peritoneal dialysis system made in accordance with the present invention.

Turning to FIG. 4, a cycler 30 includes a dialysate container 11 connected to a pump 31. The pump 31 is connected to a pressure sensor 32. The pump 31 and pressure sensor 32 are disposed in-line in a lumen 33 that connects the dialysate container 11 to a catheter 34. Control valves are provided at 35, 199. A drain container 13 is also connected to a pump 36 which is connected to a sensor 37. The pump 36 and sensor 37 are also connected in-line to a lumen 38 which connects the drain container 13 to the catheter 34. Control valves are again provided at 41, 42. During the fill, the pump 31 pumps dialysate from the container 11 through the lumen 33 and catheter 34 into the peritoneum (not shown) of the patient 12. During this time, the sensor 37 monitors and measures the intraperitoneal pressure. A signal is sent to the controller of the cycler 30 shown schematically at 43. A control panel is indicated generally at 44.

During the drain, the sensor 32 can accurately monitor and measure the intraperitoneal pressure of the patient 12. In the embodiment illustrated in FIG. 4, no pumps or control valves are disposed between the sensor 32 and the patient 12.

Turning to FIG. 5, a cycler 50 is illustrated which includes reversible pumping chambers 51, 52 with sensors 53, 54 disposed between the reversible pumping chambers 51, 52 and the patient 12 respectively. Control valves 55 and 56 are disposed on another side of the reversible pumping chamber 51 and the sensor 53 and control valves 57, 58 are provided on either side of the reversible pumping chamber 52 and sensor 54. The sensors 53, 54 actually measure the pressure on the diaphragms of the reversible pumping chambers 51, 52.

Turning to FIG. 6, a cycler 60 is illustrated with a chamber 61 for accommodating the drain container 13 and a chamber 62 for accommodating the dialysate container 11. Each chamber 61, 62 is equipped with an integrated valve assembly and pressure sensor shown at 63, 64. In the embodiment 60 shown in FIG. 6, the chamber 61 must be capable of being evacuated. Dialysate may flow from the dialysate container 11 by way of gravity or pressure fill. Again, the sensors of the valve assembly/sensor combinations 63, 64 monitor the intraperitoneal pressure of the patient 12 as discussed above.

Figure 7:
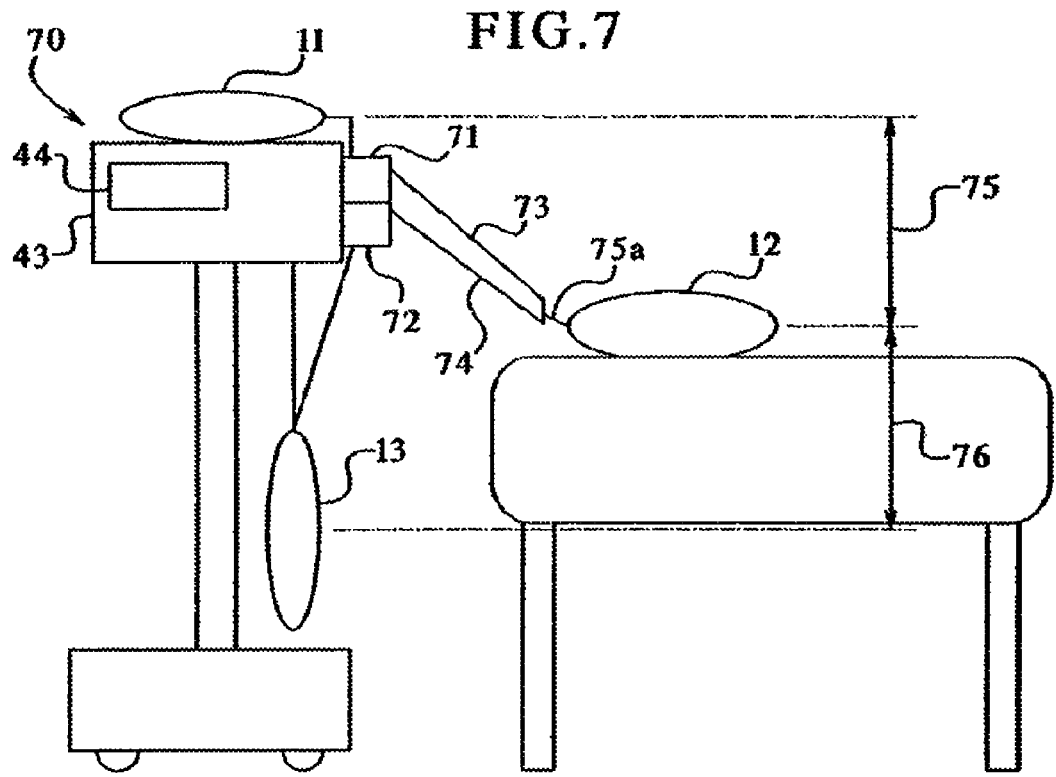
FIG. 7 illustrates, schematically, a fourth embodiment of an automated peritoneal dialysis system made in accordance with the present invention.

In the embodiment 70 illustrated in FIG. 7, the dialysate container 11 and drain container 13 are both connected to integrated control valves and pressure sensors 71, 72. Each of the integrated control valves and pressure sensors 71, 72 are connected to lumens 73, 74 respectively which are connected to the catheter 75a by way of a Y-connection. The details of all the Y-connections and clamps are not shown but are known to those skilled in the art. Flow from the dialysate container 11 to the patient is carried out under the gravitational head shown at 75 while flow from the patient to the drain container 13 is carried out under the gravitational head shown at 76.

Figure 8:
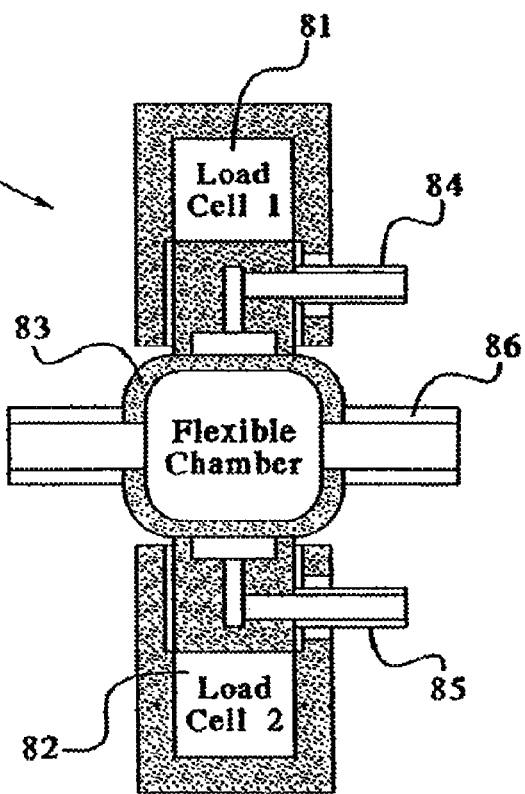
FIG. 8 illustrates a pressure sensor made in accordance with the present invention.

FIG. 8 illustrates one in-line pressure sensor 80 that is suitable for use with the present invention. Redundant load cells 81, 82 are connected to the flexible pressure sensing membrane 83 by a vacuum connected by the line 84, 85. A lumen connecting the cycler to the patient is shown at 86.

Figure 9:
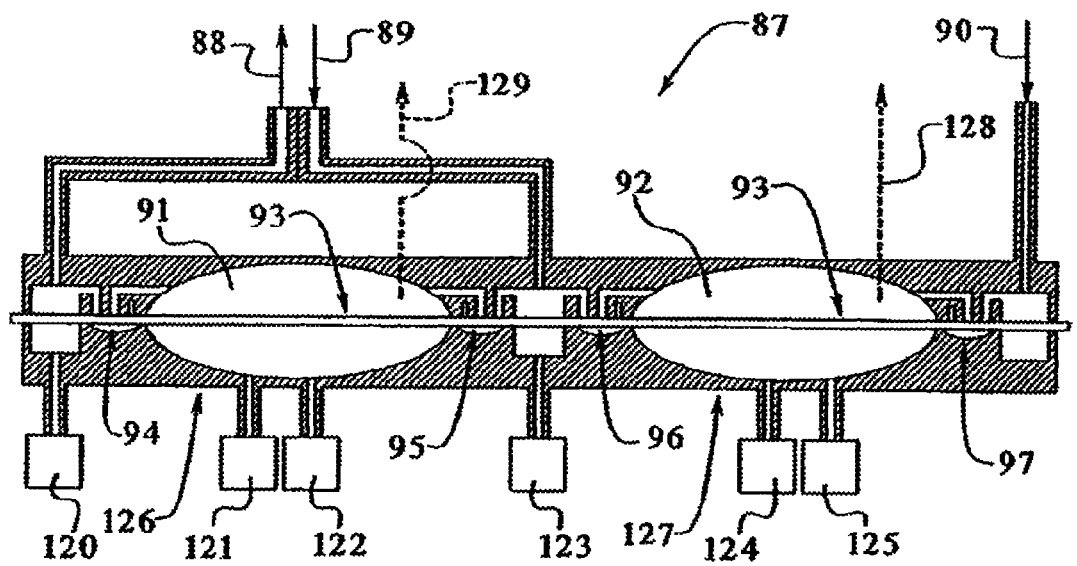
FIG. 9 illustrates a fifth embodiment incorporating dual pumping chambers and pressure sensors made in accordance with the present invention.

FIG. 9 illustrates a dual-pumping chamber cassette 87 which includes an output line 88 which connects the cassette 87 to the patient and an input line 89 connecting the patient to the cassette 87. The line 90 connects the cassette 87 to the dialysate container (not shown). Each pumping chamber 91, 92 are in communication with all three lines 88, 89 and 90. Thus, every line can be connected to either pumping chamber 91, 92. The pumping chambers 91, 92 are bound on one side by a common diaphragm shown at 93. Flow is controlled by the use of diaphragm valves shown at 94, 95, 96 and 97. Pressure sensors are shown at 120, 121, 122, 123, 124, 125. However, pressure sensors 123 and 120 are the sensors used to measure intraperitoneal-pressure in accordance with the present invention. The remaining sensors 121, 122, 124, 125 are used to monitor the operation of the pumps 126, 127.

When the left diaphragm pump 126 is pushing dialysate to the patient, the sensor 123 can measure the intraperitoneal pressure through the line 89. When the left diaphragm pump 126 is draining fluid from the patient through the line 89, the sensor 120 can measure intraperitoneal pressure through the line 88 and while the right pump 127 is pumping fluid to the drain container (not shown) through the drain line shown schematically at 128. When the right diaphragm pump 127 is being used to drain fluid from the patient, the sensor 120 can measure intraperitoneal pressure while the left diaphragm pump 126 is pumping fluid to the drain container (not shown) through the drain line shown schematically at 129.

Figure 10:
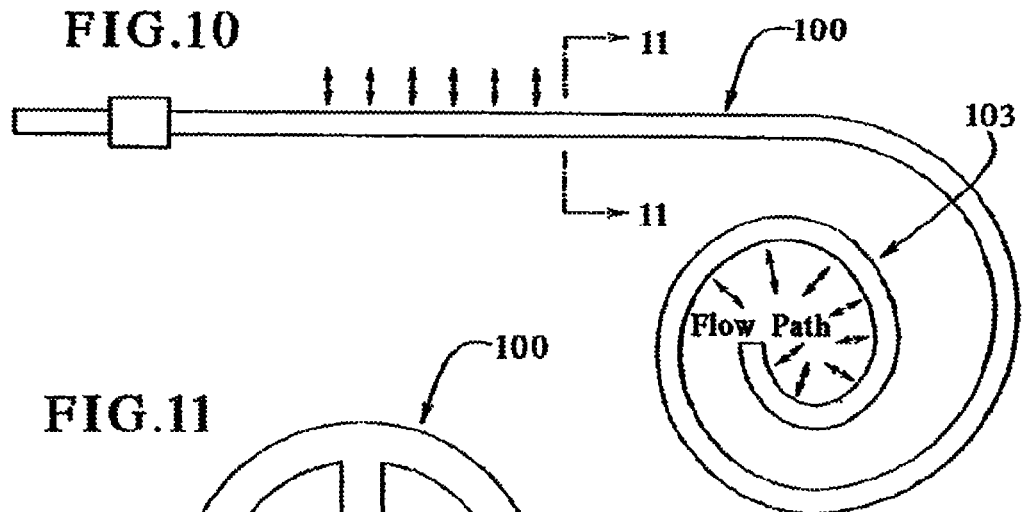
FIG. 10 illustrates, schematically, a dual lumen catheter that can be utilized with the present invention.
Figure 11:
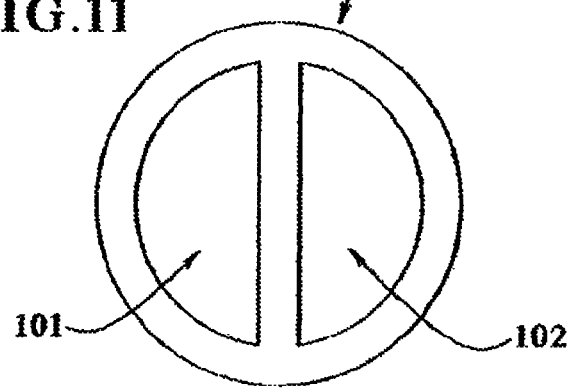
FIG. 11 is a sectional view taken substantially along line 11-11 of FIG. 10.

FIGS. 10 and 11 illustrate a dual-lumen catheter 100 which includes separate passageways 101, 102. The employment of a dual lumen catheter 100 as compared to a dual lumen patient line can move the point at which the pressure is measured to within the peritoneum itself by way of communication through the separate flowpaths 101, 102. The dual lumen catheter 100 installs like a single lumen catheter, yet will function either as a flow through or a standard catheter. Both fluid pathways 101, 102 are used to withdraw and deliver fluid during the drain and fill. While one pathway delivers fluid, the other pathway drains. The end section, shown generally at 103, is perforated.

A comparison of an APD therapy for a prior art APD cyclers and one manufactured in accordance with the present invention are summarized as follows:

| Therapy Parameter | Current APD Cycler | Cycler Using Invention |
|---|---|---|
| Total Therapy Volume | 15 liters | 15 liters |
| Fill Volume | 2.2 liters | 2.5 liters max |
| Fill Pressure Limit | not applicable | 14 mm Hg max |
| Total Therapy Time | 8 hours | 8 hours |
| Last (Day) Fill Volume | 1,500 ml | 1,500 ml |
| Last Fill Dextrose | Same | Same |
| Initial Drain Alarm | 1,200 ml | 1,200 ml |
| Drain X of N Alarm | 80% | 80% |

TABLE 1

Comparison of Therapies for Current Cylcers versus Cycler using Invention Method

| Therapy Phase | Therapy Parameter | Prior Art Cycler 1 | Prior Art Cycler 2 | Invention Cycler 3 |
|---|---|---|---|---|
| Initial Drain | Drain Volume | 1,200 ml | 1,200 ml | 1,200 ml |
| | Patient Volume | 300 ml | 300 ml | 300 ml |
| Fill 1 of 5 | Fill Volume | 2,200 ml | 2,200 ml | 2,500 ml |
| | Patient Volume | 2,500 | 2,500 | 2,800 |
| | Fill Pressure | not applicable | not applicable | 12 mm Hg |
| Drain 1 of 5 | Drain Volume | 1,800 ml | 2,200 ml | 2,200 ml |
| | Patient Volume | 700 ml | 300 ml | 600 ml |
| Fill 2 of 5 | Fill Volume | 2,200 ml | 2,200 ml | 2,400 ml |
| | Patient Volume | 2,900 ml | 2,500 ml | 3,000 ml |
| | Patient Pressure | not applicable | not applicable | 14 mm Hg |
| Drain 2 of 5 | Drain Volume | 1,800 ml | 2,200 ml | 2,200 ml |
| | Patient Volume | 1,100 ml | 300 ml | 800 ml |
| Fill 3 of 5 | Fill Volume | 2,200 ml | 2,200 ml | 2,200 ml |
| | Patient Volume | 3,300 ml | 2,500 ml | 3,000 ml |
| | Patient Pressure | not applicable | not applicable | 14 mm Hg |
| Drain 3 of 5 | Drain Volume | 1,801 ml | 2,200 ml | 2,200 ml |
| | Patient Volume | 1,499 ml | 300 ml | 800 ml |
| Fill 4 of 5 | Fill Volume | 2,200 ml | 2,200 ml | 2,200 ml |
| | Patient Volume | 3,699 ml | 2,500 | 3,000 ml |
| | Patient Pressure | not applicable | not applicable | 3,000 ml |
| Drain 4 of 5 | Drain Volume | 1,800 ml | 2,200 ml | 2,200 ml |
| | Patient Volume | 1,899 ml | 300 ml | 800 ml |
| Fill 5 of 5 | Fill Volume | uF Alarm Bypass 2,200 ml | 2,200 ml | 2,200 ml |
| | Patient Volume | 4,099 ml | 2,500 ml | 3,000 ml |
| | Patient Pressure | Patient Wakes Overfull Manually Drains 1,500 ml | not applicable | 14 mm Hg |
| Drain 5 of 5 | Drain Volume | 1,800 ml | 2,200 ml | 2,200 ml |
| | Patient Volume | 799 ml | 300 ml | 800 ml |
| Final Fill | Fill Volume | 1,500 ml | 1,500 ml | 1,500 ml |

Inspection of Table 1 shows that cycler 1 woke the patient at around 4:30 in the morning with a negative uF alarm at the beginning of Fill 5. The patient bypassed the alarm because he did not feel overrun and immediately fell back asleep. He woke up about 15 minutes later when he had difficulty breathing and felt extremely overfull. He manually drained about 1500 ml but was unable to go back to sleep. He filed a formal product complaint with the manufacturer.

The data of Table 1 shows that cycler 2 ran a completely normal therapy but the total therapy clearance (calculated based upon the sum of the night patient volumes) was only 84.5% of that obtained by cycler 3, which was using the cycler that used the method of the current invention.

The data of Table 1 shows that cycler 3 ran a completely normal therapy and that the fill volume was limited on one occasion by the maximum fill volume but on four occasions by the patient's intraperitoneal pressure. This patient never felt any discomfort and had no alarms during the night. The limit on the IPP prevented him from being overfilled even though he had successive drains that were not complete. The volume of fluid in his peritoneum never exceeded 3 liters.

The patient on cycler 1 had an intraperitoneal pressure in excess of 14 mm Hg during dwells 3 and 4. His breathing may have been impaired and his heart may have had to work harder but the discomfort was not enough to wake him up from a sound sleep until it peaked at 4,099 ml during dwell 5.

In conclusion, the method of the present invention provides for optimum fills and therefore more clearance while preventing overfills that bring discomfort and inhibit the function of vital body organs. A negative uF alarm would seldom occur because overfills of the required magnitude would be prevented by the IPP sensors.

Calculation of Intraperitoneal Pressure (IPP)

In order to calculate the IPP, one may first calculate the patient head height correction using conservation of energy:

$$\Delta(\tfrac{1}{2}\rho V^2 + P - \rho a_g h) + \text{Frictional Losses} = 0$$

The velocity V of fluid through the patient line is the same at both ends of the line as is the fluid density, so this equation can be written as $$(P_2 - P_1) - \rho a_g (h_2 - h_1) + \text{Frictional Losses} = 0$$

which can be rearranged as $$\Delta h = \frac{(P_1 - P_2) - \text{Frictional Losses}}{\rho a_g}$$

Example 1

P1=1.25 psig=85060 (gram/cm)/(cm²-sec²)
P2=0.9 psig=61240 (gram/cm)/(cm²-sec²)
Frictional Losses=39130 (gram/cm)/(cm²-sec²) with flow of 197 cmn/min in a 4 mm ID line at a velocity of approximately 172 cm/sec, wherein $a_g 981 \text{ cm/sec}^2$ $\rho = 1 \text{ gram/cm}^3$ $$\Delta h = \frac{((85060 - 61240) - 39130)(\text{gram/cm})/(\text{cm}^2 - \text{sec}^2)}{1 \text{ gram/cm}^3 * 981 \text{ cm/sec}^2}$$

$\Delta h = -15.6$ cm (The patient is 15.6 cm below the membrane)

Example 2

P1=1.25 psig=85060 (gram/cm)/(cm²-sec²)
P2=0.45 psig=30620 (gram/cm)/(cm²-sec²)
Frictional Losses=39130 (gram/cm)/(cm²-sec²) with flow of 197 cmn/min in a 4 mm ID line at a velocity of approximately 172 cm/sec, wherein $a_g 981 \text{ cm/sec}^2$ $\rho = 1 \text{ gram/cm}^3$ $$\Delta h = \frac{((85060 - 30620) - 39130)(\text{gram/cm})/(\text{cm}_2 - \text{sec}^2)}{1 \text{ gram/cm}^3 * 981 \text{ cm/sec}^2}$$

$\Delta h = +15.6$ cm (The patient is 15.6 cm above the membrane)

The patient head height can be established at the beginning of each fill. Any changes in the head height that occur during the fill can be attributed to an increase in intraperitoneal pressure (IPP) since the patient is asleep.

Figure 12:
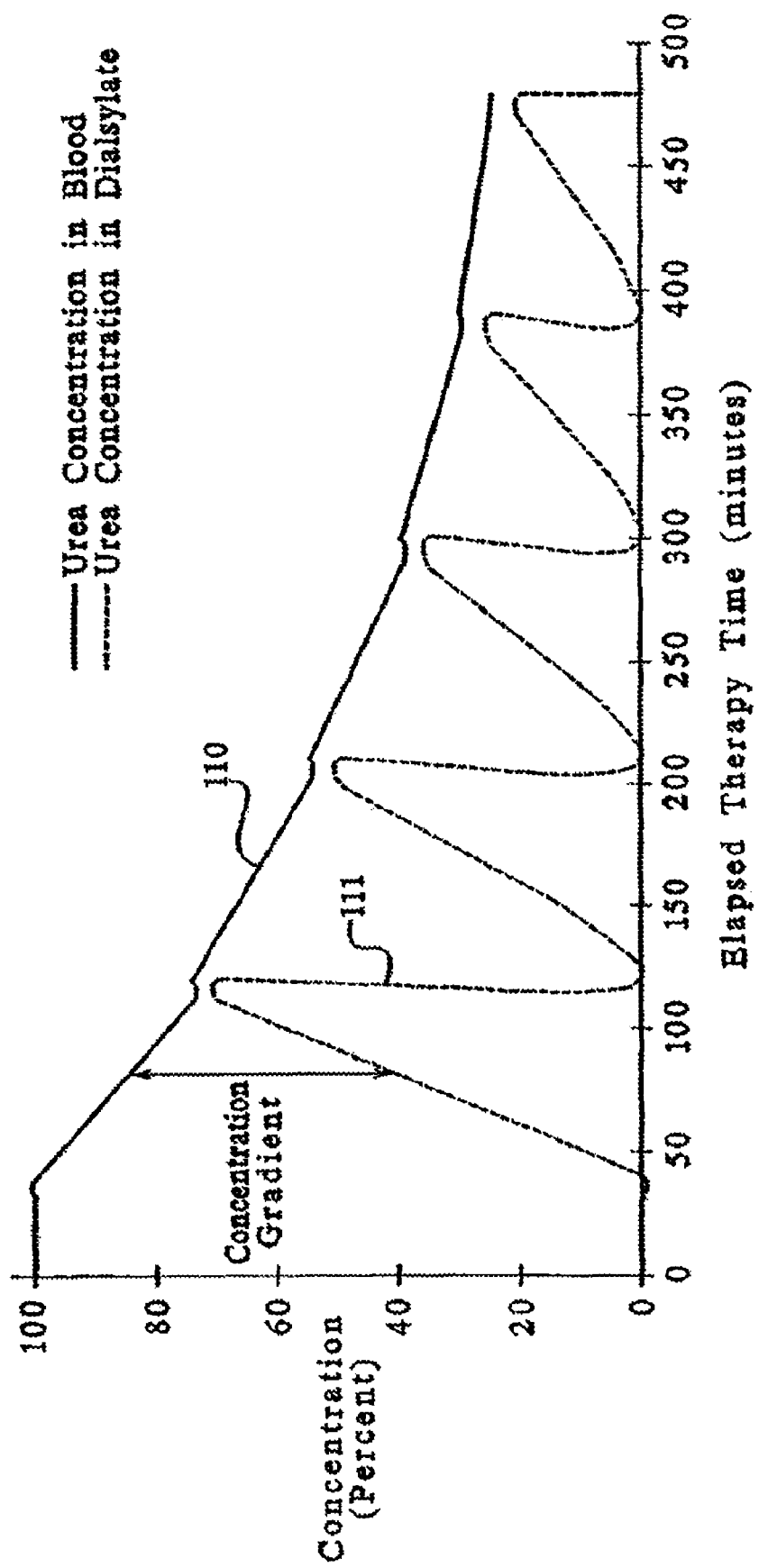
FIG. 12 illustrates, graphically, the urea concentration in blood and the urea concentration in a dialysate during a multiple dwell dialysis session.
Figure 13:
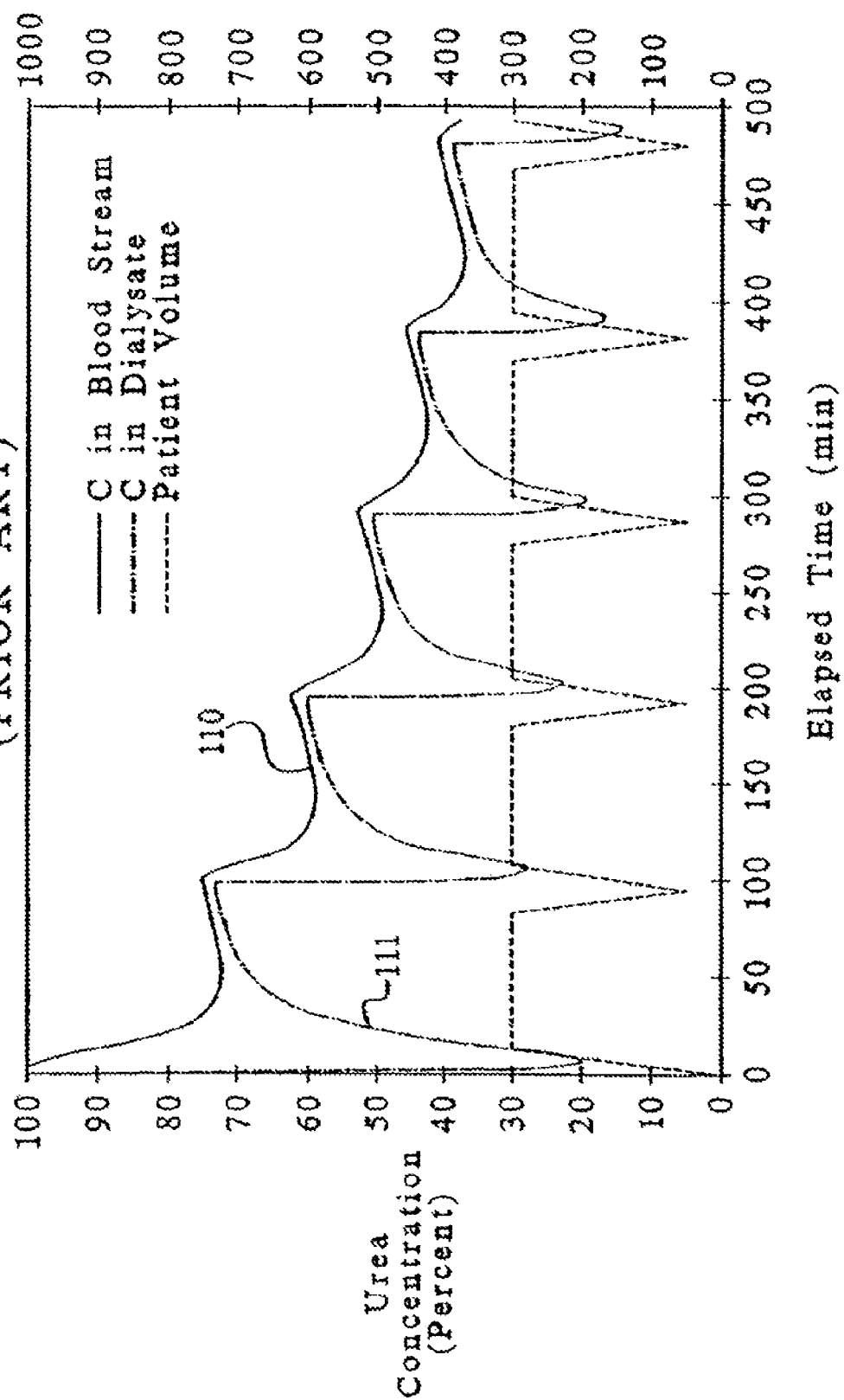
FIG. 13 illustrates, graphically, the concentration of urea in a patient's bloodstream versus the concentration of urea in a dialysate solution for an automated peritoneal dialysis solution practiced in accordance with the prior art.
Figure 14:
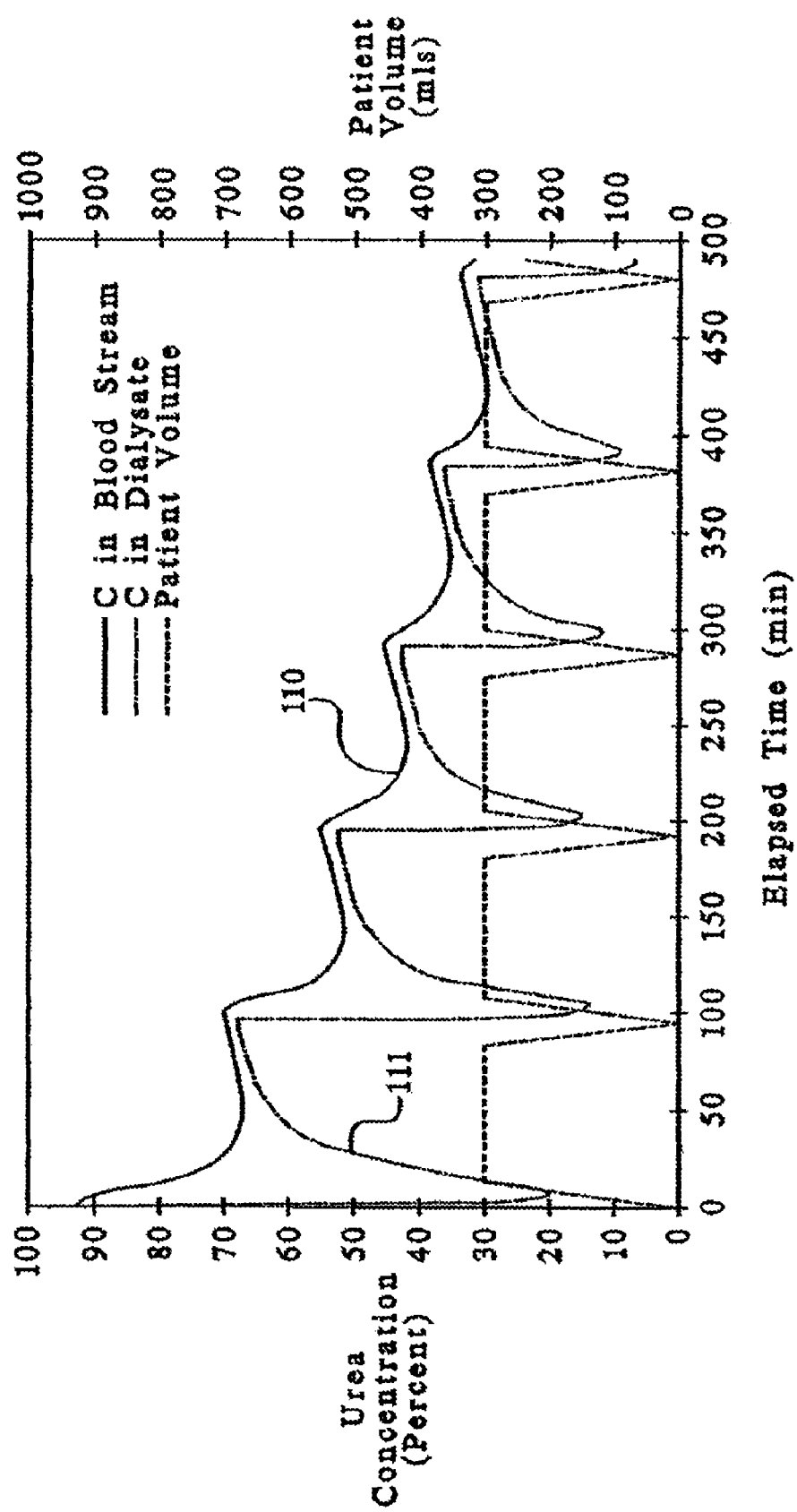
FIG. 14 illustrates, graphically, the concentration of urea in a patient's bloodstream versus the concentration of urea in a dialysate for an automated peritoneal dialysis therapy session carried out in accordance with the present invention.

Turning to FIG. 12, the concentration gradient between the urea concentration 110 in the patient's blood and the urea concentration 111 in the dialysate for typical APD cyclers is illustrated graphically. Comparing the results illustrated in FIGS. 13 and 14, it is evident that APD cyclers equipped with the sensors of the present invention provide superior results. Specifically, the data illustrated graphically in FIG. 13 was obtained using a prior art APD cycler. The data obtained in FIG. 14 was obtained using an APD cycler utilizing two sensors for monitoring intraperitoneal pressure. Note that the urea concentration 110 in the bloodstream is lower in FIG. 14 than in FIG. 13. Further note, the dialysate volume or fill volume is lower for the therapy illustrated in FIG. 14 than the therapy illustrated in FIG. 13. Thus, the present invention provides improved urea clearance with lower fill volumes.

It should be understood that various changes and modifications to the presently preferred embodiments described herein will be apparent to those skilled in the art. Such changes and modifications can be made without departing from the spirit and scope of the present subject matter and without diminishing its intended advantages. It is therefore intended that such changes and modifications be covered by the appended claims.

The invention is claimed as follows:

1. A peritoneal dialysis system comprising:
a removable cassette defining first and second flexible pump chambers and first and second pressure sensing areas that are fluidly connected to the first and second pump chambers, respectively; and
a peritoneal dialysis machine configured to secure the removable cassette, the peritoneal dialysis machine including
(i) first and second pumps configured to be moved relative to the removable cassette to force peritoneal dialysis fluid out of the first removable pump chamber into a peritoneal cavity of a patient, and draw peritoneal dialysis fluid into the second removable pump chamber during operation of the peritoneal dialysis system,
(ii) first and second pressure sensors positioned to align with and to contact the first and second pressure sensing areas, respectively, of the removable cassette when the removable cassette is secured within the peritoneal dialysis machine, and
(iii) a controller connected to the first and second pressure sensors and adapted to change the operation of the peritoneal dialysis machine in response to changes in pressure sensed by the pressure sensors, wherein the first and second pressure sensors and the first and second pressure sensing areas are arranged so that the first pressure sensor measures a pressure of fluid in a first fluid passage between the first pump chamber and the patient during operation of the peritoneal dialysis system, and the second pressure sensor measures a pressure of fluid in a fluid passage between the second pump chamber and the patient during operation of the peritoneal dialysis system.

2. The peritoneal dialysis system of claim 1, wherein at least one of the pressure sensing areas of the removable cassette is sucked to at least one of the first and second pressure sensors during operation of the peritoneal dialysis system.

3. The peritoneal dialysis system of claim 1, wherein at least one of the pressure sensing areas of the removable cassette is directly contacted by at least one of the first and second the pressure sensors during operation of the peritoneal dialysis system.

4. The peritoneal dialysis system of claim 1, wherein the controller is adapted to determine a patient pressure based on a pressure measured by at least one of the first and second pressure sensors.

5. A peritoneal dialysis system comprising:
a removable cassette defining a flexible pump chamber and a pressure sensing area that is fluidly connected to the pump chamber wherein, during operation of the peritoneal dialysis system, peritoneal dialysis fluid is contained in the pump chamber for delivering the dialysis fluid to a peritoneal cavity of a patient; and
a peritoneal dialysis machine configured to secure the removable cassette, peritoneal dialysis machine including
(i) a pressure sensor positioned to align with and to contact the pressure sensing area of the removable cassette when the removable cassette is secured to the peritoneal dialysis machine, and
(ii) a controller connected to the pressure sensor and adapted to change the operation of the peritoneal dialysis machine in response to changes in pressure sensed by the pressure sensor, wherein the pressure sensor and the pressure sensing area are arranged so that the pressure sensor measures a pressure of fluid in a fluid passage between the pump chamber and the patient during operation of the peritoneal dialysis system.

6. The peritoneal dialysis system of claim 5, wherein the pressure sensing area of the removable cassette is fluidly connected to the pump chamber via a channel formed in the removable cassette.

7. The peritoneal dialysis system of claim 6, wherein the channel that fluidly connects the pressure sensing area to the pump chamber is narrower than the pressure sensing area and the pump chamber.

8. The peritoneal dialysis system of claim 5, wherein the removable cassette has a second pump chamber and a second pressure sensing area in fluid communication with the second pump chamber, and wherein the peritoneal dialysis machine includes a second pressure sensor positioned to align with and to contact the second pressure sensing area of the removable cassette when the cassette is secured to the peritoneal dialysis machine, and wherein the second pressure sensor and the second pressure sensing area are arranged so that the second pressure sensor measures a pressure of fluid in a fluid passage between the second pump chamber and the patient during operation of the peritoneal dialysis system, and wherein the controller is connected to the second pressure sensor and adapted to change the operation of the peritoneal dialysis machine in response to changes in pressure sensed by the second pressure sensor.

9. The peritoneal dialysis system of claim 5, wherein the removable cassette further includes a plurality of fluid channels and a plurality of valves each associated with a corresponding one of the fluid channels, wherein the valves are each operable to inhibit fluid flow through a corresponding one of the fluid channels.

10. The peritoneal dialysis system of claim 5, wherein the controller is adapted to determine a patient pressure based on a pressure measured by the pressure sensor.

11. The peritoneal dialysis system of claim 5, wherein the pressure sensing area of the removable cassette is sucked to the pressure sensor during operation of the peritoneal dialysis system.

12. The peritoneal dialysis system of claim 5, wherein the pressure sensor includes a pair of load cells.

13. The peritoneal dialysis system of claim 5, wherein the pressure sensing area of the removable cassette is directly contacted by the pressure sensor during operation of the peritoneal dialysis system.

14. A peritoneal dialysis system comprising:
a peritoneal dialysis machine including a pressure sensor; and
a peritoneal dialysis cassette operable with the peritoneal dialysis machine, the peritoneal dialysis cassette including
a flexible pump chamber adapted to contain a fluid;
ingress and egress passageways fluidly connected to the pump chamber to conduct fluid into and out of the pump chamber to and from a peritoneal cavity of a patient; and
a pressure sensing area fluidly connected to the pump chamber, wherein an outer surface of the pressure sensing area of the cassette is positioned to align with and to contact the pressure sensor of the peritoneal dialysis machine when the cassette is positioned within the peritoneal dialysis machine so as to enable the pressure sensor to measure the pressure of fluid in one of the ingress and egress passageways between the pump chamber and the patient during peritoneal dialysis,
wherein operation of the peritoneal dialysis machine is adapted to change in response to changes in pressure sensed by the pressure sensor.

15. The peritoneal dialysis system of claim 14, wherein the peritoneal dialysis cassette further includes a second flexible pump chamber adapted to contain fluid, second ingress and egress passageways fluidly connected to the second pump chamber to conduct fluid into and out of the second pump chamber to and from the patient, and a second pressure sensing area in fluid communication with the second pump chamber, wherein an outer surface of the second pressure sensing area of the cassette is positioned to align with and to contact a second pressure sensor of the peritoneal dialysis machine when the cassette is positioned within the peritoneal dialysis machine so as to enable the second pressure sensor to measure the pressure of fluid in one of the second ingress and egress passageways between the second pump chamber and the patient during peritoneal dialysis.

16. The peritoneal system of claim 14, wherein the surface of the pressure sensing area is enlarged.

17. The peritoneal system of claim 14, wherein the peritoneal dialysis cassette further includes a plurality of valves each associated with a corresponding one of the ingress and egress passageways, wherein the valves are each operable to inhibit fluid flow through a corresponding one of the ingress and egress passageways.

18. The peritoneal system of claim 14, wherein the pressure sensing area of the cassette is located along one of the ingress and egress passageways of the disposable cassette.

19. The peritoneal dialysis system of claim 14, wherein the pressure sensing area of the cassette is fluidly connected to the pump chamber.

20. The peritoneal dialysis system of claim 14, wherein the pressure sensing area of the cassette is sucked to the pressure sensor to measure the pressure of fluid in one of the ingress and egress passageways between the pump chamber and the patient during peritoneal dialysis.

* * * * *